Figure 1:
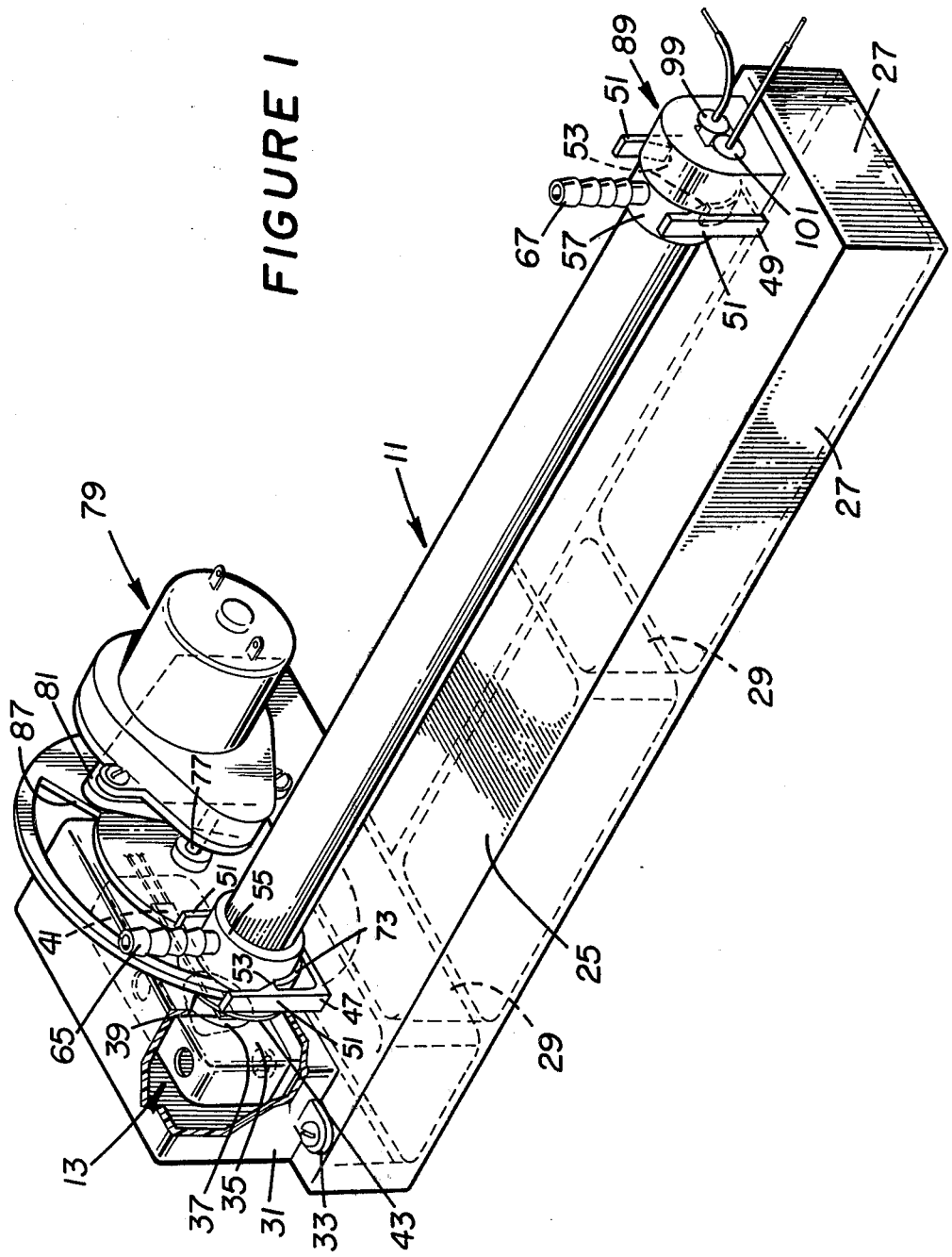

United States Patent [19]

Passaro et al.

[11] 4,346,296
[45] Aug. 24, 1982

[54] NON-DISPERSIVE INFRARED GAS ANALYZER

[75] Inventors: Robert E. Passaro, Walnut Creek; Kevin Williams, Pinole, both of Calif.

[73] Assignee: Andros Analyzers Incorporated, Oakland, Calif.

[21] Appl. No.: 178,302

[22] Filed: Aug. 15, 1980

[51] Int. Cl.³ .......................................... G01N 21/26
[52] U.S. Cl. ................................................. 250/343
[58] Field of Search ............... 250/343, 344, 345, 373, 250/432 R, 435; 356/246, 438, 440

[56] References Cited

U.S. PATENT DOCUMENTS

| | | | |
|---|---|---|---|
| 3,953,734 | 4/1976 | Dimeff | 250/343 |
| 4,013,260 | 3/1977 | McClatchie et al. | 250/343 |
| 4,163,899 | 8/1979 | Burough | 250/343 |
| 4,175,233 | 11/1979 | DePalma et al. | 250/343 |
| 4,220,415 | 9/1980 | Staab et al. | 250/343 X |

*Primary Examiner*—Davis L. Willis
*Attorney, Agent, or Firm*—Fitch, Even, Tabin, Flannery & Welsh

[57] ABSTRACT

A non-dispersive infrared gas analyzer is described. Infrared energy is directed through a sample cell, and is interrupted at a predetermined frequency. The infrared energy at at least one preselected wavelength is detected to produce an AC signal having an amplitude proportional to the infrared energy passing through said sample cell and having a frequency corresponding to the predetermined frequency. The preselected wavelength corresponds to the characteristic absorption wavelength of a preselected gas. This AC signal is processed to produce a DC signal having an amplitude proportional to the concentration of the preselected gas in the mixture being analyzed. The signal processor includes an output amplifier, a voltage biasing network including a summing junction connected to the input of the amplifier, and a first variable control manually adjustable to bring the current at the summing junction to zero in the presence of a non-absorbing gas in the sample cell. A second variable control is connected in a feedback loop from the output of the amplifier to the input thereof for span calibration.

11 Claims, 2 Drawing Figures

NON-DISPERSIVE INFRARED GAS ANALYZER

This invention relates generally to gas analyzers of the non-dispersive infrared type. More particularly, the invention relates to an improved gas analyzer and gas analyzing method which provides for extremely low cost while retaining acceptable accuracy for many applications.

Non-dispersive infrared gas analyzers typically utilize an infrared source to produce and direct infrared energy through an unknown gas mixture contained in a sample cell. The energy passing through the sample cell is detected and electrical signals are produced representative thereof. These signals are processed to produce an output indicating the concentration of one or more of the constituents of the gas in the sample cell.

Such gas analyzers utilize the principle that various gases exhibit substantial absorption characteristics at specific wavelengths in the infrared radiation spectrum. A gas analyzer of this type is shown and described in U.S. Pat. No. 4,013,260, McClatchie et al., issued Mar. 22, 1977, and assigned to the assignee of the present invention. Another type of non-dispersive infrared gas analyzer is shown and described in U.S. Pat. No. 3,953,734, Dimeff, issued Apr. 27, 1976, and assigned to the United States of America.

In both of the above cited patents, and in similar types of infrared gas analyzers, the beam of infrared energy passing through the sample cell containing the unknown gas mixture is varied by the interposition of one or more filters in the path of the light beam. Typically, each filter passes only radiation at the characteristic absorption wavelength of a particular gas of interest. Another filter may also be used as a reference filter at a wavelength close to but not overlapping the characteristic absorption wavelength of any of the gases present in the sample cell.

Gas analyzers of the foregoing described type exhibit high accuracy from so-called drift. Such drift can occur as a result of contamination on the windows in the sample cell which will attenuate the radiation passing therethrough and which could be interpreted erroneously as indicating the presence of the gas to be detected in the gas sample. Moreover, shifts in the output of the detector, inherent in many detector constructions, and temperature changes in the source of the infrared radiation, can provide similar changes or drift.

Such prior art devices typically require the generation of some type of synchronizing signal in order to coordinate the operation of the signal processing circuitry with the rotation of the filter wheel.

A more simple type of gas analyzer, rather than employing a rotary filter wheel, utilizes a stationary filter or filters with associated detectors and produces an AC signal on the detector by periodically interrupting the infrared beam, such as with a rotary chopper. Nevertheless, the problems of drift previously described as being associated with rotary filter wheel type gas analyzers are also present in so-called chopper type gas analyzers. Dealing with such phenomenon has increased the cost of such gas analyzers because of the inclusion of some type of comparison or reference signal, or other form of drift compensation. Such gas analyzers have also frequently employed the generation of synchronizing signals in order to synchronize the processing electronics with the motion of the chopper wheel.

It is an object of the present invention to provide an improved gas analyzer.

Another object of the invention is to provide a gas analyzer which is extremely low in cost and simple of operation.

Another object of the invention is to provide a non-dispersive infrared gas analyzer which is low in cost and simple of construction, and yet which provides acceptable compensation for drift without affecting span stability.

Figure 2:
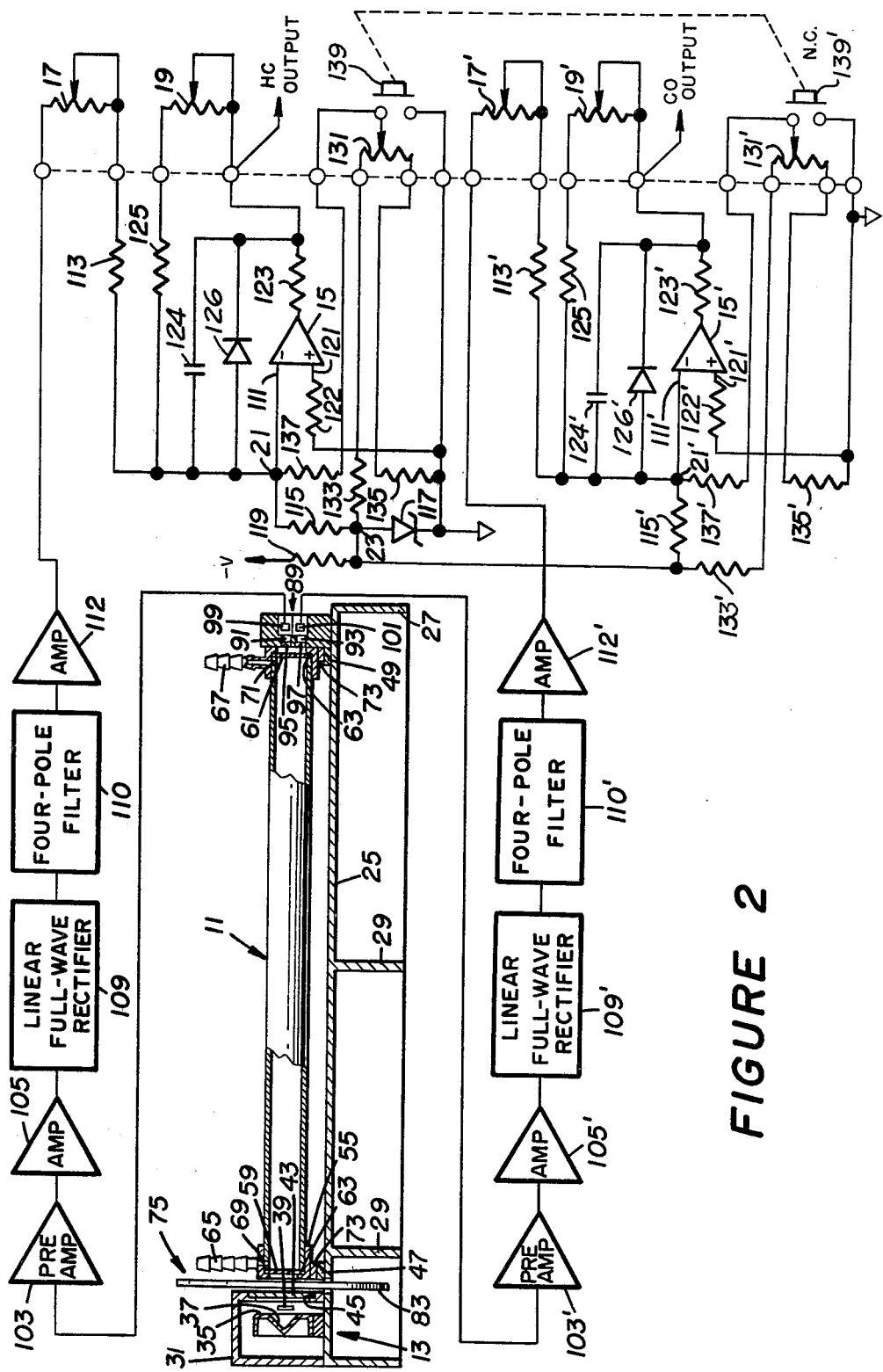

Other objects of the invention will become apparent to those skilled in the art from the following description, taken in connection with the accompanying drawings wherein:

FIG. 1 is a perspective view of a gas analyzer constructed in accordance with the invention; and FIG. 2 is a schematic diagram, with part in full section, of the gas analyzer of FIG. 1.

Very generally, the non-dispersive infrared gas analyzer of the invention comprises a sample cell 11 for containing the gas mixture to be analyzed. Means 13 direct infrared energy through the sample cell and the infrared energy is periodically interrupted at a predetermined frequency. A detected signal is produced corresponding to the infrared energy at at least one preselected wavelength, such signal being an AC signal having an amplitude proportional to the infrared energy passing through the sample cell at that wavelength and having a frequency corresponding to the predetermined frequency. The preselected wavelength corresponds to the characteristic absorption wavelength of the gas it is desired to detect in the sample mixture. The AC signal output of the detector is processed to produce a DC signal having an amplitude proportional to the concentration of the gas to be detected. The signal is full wave rectified and applied to an amplifier 15. The output signal amplitude of the amplifier is read as the gas concentration. A first variable resistor 17 is series connected with the input of the amplifier and a second variable resistor 19 is series connected between the output and the input of the amplifier to feed back signals from the output to the input thereof. The input of the amplifier is connected to a summing junction 21 which, in turn, is connected to a source of reference potential −V via junction 23. Reference potential −V is opposite in polarity to the signal applied to the summing junction by the first variable resistor 17. Adjustment of the first variable resistor 17 serves to adjust the signal at the summing junction and when the output signal of the amplifier 15 is adjusted to zero in the absence of the gas to be detected in the sample chamber, the analyzer is compensated for span drift. Variation in span calibration is inherently avoided because of the connection of the variable resistor 17.

Referring now more particularly to the drawings, there is illustrated a device constructed in accordance with the invention for detecting the presence of two gases in the exhaust gas of an automobile engine. The two gases may be hydrocarbon and carbon monoxide, but the invention is not limited to use in connection with such specific gases, nor is it limited to use in connection with the exhaust gas of an automobile engine. There will be other uses, apparent to those skilled in the art, for the analyzer of the invention where a low cost unit of the type described will be acceptable.

The unit is mounted on a base plate 25 having a generally rectangular shape and having rigidizing walls 27 at its periphery connected by rigidizing cross webs 29.

At one end of the unit, the infrared source 13 is shown mounted in a source housing 31 secured to the base plate by mounting brackets 33. The source 13 includes a reflector plate 35 having a reflecting recess 37 of parabolic, conical or other suitable shape to reflect the infrared energy into a beam. The source element 39, which may be of any suitable type, is mounted by a holder 41. Suitable electrical connection is made to the source element by means, not shown. A 43 window is provided spanning an opening 45 in the source housing 31. The window may be of any material substantially transparent to infrared radiation at the wavelengths of interest.

The sample cell 11 is mounted on a pair of roughly U-shaped mounting clips 47 and 49 attached to the base plate and is in alignment with the infrared energy eminating from the infrared source 13. Each of the clips 47 and 49 comprises a pair of upright tines 51 which are resilient and which have projections 53 extending inwardly therefrom. As will be described below, the resilient tines enable sample cell to be easily removed from the device for replacement or cleaning. Each end of the sample cell is provied with an end sleeve 55 and 57, respectively, each of which retains in place a window 59 and 61, respectively, transparent to infrared radiation. A suitable material for the windows is, for example, Teflon (a trademark of DuPont). Each of the end sleeves has an annular shoulder 63 which projects internally to engage the outer surface of the corresponding window 59 or 61. A nozzle, 65 and 67, respectively, is mounted in each end sleeve 55 and 57, for permitting exhaust gas to pass into and out of the sample cell from the automobile engine being analyzed. The sample cell has openings 69 and 71 aligned with the nozzles 55 and 57, respectively, to provide the necessary communication.

Each of the sleeves 55 and 57 is provided with a semi-annular collar 73 which wraps 180° around the underside of each sleeve and extends axially one half the length of the sleeve. The collars, with the sample cell 11 in the operative position, engage the underside of the projections 53, to retain the sample cell in place. However, since the sample cell will, during use, become dirty from the exhaust gas being analyzed, it is desirable that it be easily cleaned or even replaced. By merely separating the tines 51 so the projections 53 clear the collars 73, the sample cell may be easily removed or installed.

The end of the sample cell assembly adjacent the source block is spaced a short distance therefrom so as to enable the interposition of a chopper wheel 75. The chopper wheel 75 is rotatably mounted on the spindle 77 of a drive motor 79 which, in turn, is mounted to the base plate 25 by a motor mount bracket 81. The chopper wheel 75 comprises a circular opaque disk which may be of any suitable construction to periodically interrupt the infrared energy eminating from the source. However, it is preferred that the disk have a cut-out region 87 of generally arcuate shape extending through 180° of the wheel rotation. In this way, the beam is blocked 50% of the time during each rotation. The chopper thus provides an AC signal which has the effect of cancelling out any background DC radiation. Of course, other types of chopper wheels may be used, such as two 90° cut-out regions, to provide the same duty cycle.

The end of the sample cell opposite the source is abutted flush against a filter and detector block 89. The block 89 is secured by suitable means to the base plate. The block 89 is generally cylindrical in shape and is axially aligned with the sample cell 11. The block 89 contains a pair of windows or openings 91 and 93 disposed side by side in alignment with radiation passing through the sample cell. A filter 95 and 97, respectively, is disposed in each of these openings to pass infrared energy of the characteristic absorption wavelengths of the gases of interest, for example, hydrocarbons and carbon monoxide.

Immediately behind the filters are mounted the two detectors 99 and 101 which may be of any suitable construction. The detectors provide an output which is proportional to the magnitude of the infrared energy passing through the corresponding filter 95 or 97. Thus, the output of each of the detectors comprises an AC signal, the amplitude of which is proportional to the energy passing through the sample cell.

Referring now more particularly to FIG. 2, a specific form of the signal processor used in the apparatus of the invention is shown. The output of the detector 99, which is a square wave signal having the frequency of the rotation of the chopper wheel 75, varies between nearly zero and a negative (or positive) voltage. This signal is applied to the preamplifier 103 in which it is suitably amplified and then passed along to a further amplification stage 105.

Following the further amplification and filtering, the signal is passed to a full wave linear rectifier 109 where the signal is rectified, and then filtered by a four-pole filter 110. The result is a DC output having an amplitude proportional to the output of the detector. This DC signal is amplified by an amplifier 112 and is applied to the negative input 111 of the amplifier 15. The input circuitry for the output amplifier 15 includes a pair of summing resistors 113 and 115, each having one end connected to the summing junction 21. The end of the summing resistor 113 opposite the summing junction is connected with the variable resistor 17 in series to the output of the amplifier 112. The other summing resistor 115 is connected to a zener diode 117, which is connected to ground. The junction between the second summing resistor 115 and the zener diode 117 is connected through a resistor 119 to the source 23 $-V$ of negative voltage. The component values are suitably selected so that variation in the resistance of the variable resistor 17 can adjust the current into the summing junction, and hence the voltage output of the amplifier 15.

The amplifier 15 has its positive input 121 grounded through a resistor 122 and its negative input 111, as previously stated, is connected to the summing junction. The output of the amplifier 15 is connected through a stabilizing resistor 123 to the meter or other indicating device (not shown) used to indicate the gas concentration. The variable resistor 19 is connected to feedback signals from the output side of the amplifier to the summing junction 21 at the negative input of the amplifier through a suitable ballast resistor 125. A capacitor 124 and a diode 126 may be connected across the amplifier 15 for reasons of stabilization.

A test circuit is provided for calibration. This circuit includes a variable resistor 131 connected through a ballast resistor 133 and the resistor 119 to the negative potential source 23 $-V$. The other end of the resistor is grounded through a resistor 135. The pick-off of the resistor 131 is connected through a resistor 137 to the summing junction 21. A normally closed test switch 139 connects the pick-off of the resistor 131 to ground.

After manufacturing the device, the output is first adjusted to zero in the presence of a non-absorbing gas, such as nitrogen. Then, a suitable calibration gas of known concentration is introduced into the sample cell at the factory. Adjustment of the variable feedback resistor 19 while observing the output voltage of the device on a suitable meter thus enables the device to be appropriately calibrated to indicate the known concentration of the calibration gas. After this calibration step is formed, no further similar calibration is necessary by the operator of the device for reasons which will be explained.

When the device is to be used to analyze the exhaust gas of an automobile engine, the operator of the device performs the initial zeroing function using a non-absorbing gas in the sample cell. In doing this, with air in the sample cell and the device turned on, the variable resistor or zeroing resistor 17 is adjusted so that the current through the feedback resistor 19 is zero. Correspondingly, the output of the amplifier will be zero and the meter reading will be zero. Then, the automobile engine is appropriately connected to pass the exhaust through the sample cell.

Once the exhaust gas begins to flow into the sample cell, concentration of the particular gas to be detected will cause a corresponding decrease in the detector output. This is processed as a decrease in the voltage applied to the variable resistor 17, resulting in a corresponding increase in current through the feedback resistor 19. The output of the amplifier 15 provides a direct indication of the particular gas concentration of interest in the sample cell.

In actual operation of the device, the output of the amplifier 112 will be affected because of changes in the overall gain of the system, and in particular by variations in the elements in the optical path. Particular detector responsiveness may vary significantly with ambient temperature. Moreover, the source radiation intensity is also a function of its temperature. The optical reflection of the interior walls of the sample cell and the optical transparency of the windows and filters will also have an effect on system gain. Slight changes in alignment of the various elements may also have an effect on overall system gain. Variations in system gain because of the above factors are commonly referred to as drift.

In order to compensate for drift, many prior art devices employ a standard or reference signal to which the particular gas signal is compared. The ratioing will typically eliminate many of the effects of drift. Such a comparison, however, requires an additional channel and additional processing circuitry, which adds significantly to the complexity and cost of the device.

In the system of the invention, prior to a use of the device, adjustment is made of the variable resistor 17 to adjust the gain of the amplifier 15 to zero the current through the feedback resistor 19. The span calibration resistor has been previously set at the factory in accordance with a test gas of known concentration. After zeroing, introduction of a gas mixture to be examined to the sample cell results in an attenuation of the signal at the detector assuming the gas of interest is present in the mixture. A corresponding increase at the output of the amplifier 115 will result. Since the amplifier gain has been adjusted by adjustment of the resistor 17, losses in system gain by optical attenuation and other factors is compensated. The system therefore is compensated for any so-called span drift. At the same time, the span calibration will remain accurate.

More particularly, if the voltage input to the variable resistor 17 ($R_O$) is designated $V_O$ when a non-absorbing gas such as nitrogen or air is introduced into the sample cell, this voltage ($V_O$) will be proportional to the product $T_1 K$ where $T_1$ is the transmitted radiation through the gas cell with a non-absorbing gas and where K is the system gain preceeding $R_O$. When an absorbing gas is introduced into the cell, at a known concentration for calibration, the DC voltage at the input to resistor 17 ($V_G$) is proportional to the transmitted radiation through the gas cell with an absorbing gas of a particular concentration ($T_2$) and also the factors $T_1$ and K mentioned above. In fact, $$V_G = T_1 K (1 - A)$$

where A is the amount of absorption of a gas of a particular concentration. Substituting $V_O$ for $T_1 K$ in this relationship, one arrives at the equation $$V_G = V_O (1 - A).$$

Thus, the gas signal $V_G$ is proportional to $V_O$ and is a linear function of the amount of absorption, A. However, $V_O$ is affected by drift because of the factor K mentioned above.

The output voltage of the device may be expressed by the equation:

$$V_{out} = -\left(\frac{V}{R_0} + \frac{V_R}{R_R}\right) R_S$$

where V is the input voltage to the resistor 17, $R_O$ is the sum of the values of the resistor 17 and 113, $V_R$ is the reference voltage at the zener diode 117, $R_R$ is the value of the reference resistor 115, and $R_S$ is the value of the span resistor 19 and 125 in series. In zeroing the instrument, a non-absorbing gas is introduced into the sample cell so that A is equal to zero. If V is to equal $V_O$ and the output voltage is to also equal zero, then, from the above equation, $$(V_O/R_O) = -(V_R/R_R).$$

Since $V_O$ is relatively unstable due to the variation in K, when the value of $R_O$ is adjusted such that the ratio $(V_O/R_O)$ is a constant and equal to $-(V_R/R_R)$ we are ready to introduce the unknown absorbing gas to the sample cell. Since $V_G$, the unknown absorbing gas, is equal to $V_O (1-A)$ one finds that the output of the device may be expressed as:

$$V_{out} = -\left(\frac{V_0(1-A)}{R_0} + \frac{V_R}{R_R}\right) R_S.$$

Solving this equation, one may write:

$$V_{out} = -\left(-\frac{V_R}{R_R}(1 - A - 1)\right) R_S = -\left(\frac{V_R}{R_R} A\right) R_S.$$

This equation may be further reduced to:

$$V_{out} = -\frac{V_R}{R_R} A R_S.$$

It may be seen that the output of the system is thereby unaffected by drift once the system is zeroed. Rather, the only variable is the factor A, the amount of attenuation provided by the unknown gas. The factor $R_S$, the span adjustment, remains unaffected by the adjustment of the resistor 17, thereby insuring that calibration remains accurate. If the first channel is for carbon monoxide, a second channel for hydrocarbons may be provided, for example. This is shown in the drawings with primed numbers for components with similar function.

For the purposes of checking span calibration, the normally closed test button switch 139 is provided. Depression of the button opens the switch 139, establishing a fixed current into the summing junction 21. This establishes a fixed current through resistors and thus produces a fixed output voltage. This voltage is then checked on the output meter or other indicator, not shown, and the span resistor 19 is suitably adjusted to recalibrate the instrument.

It will be seen, therefore, that the invention provides an improved gas analyzer which is substantially low in cost and simple of construction. Ready cleaning or even replacement of the sample cell is accomplished, and replacement units may be of extremely low cost. Moreover, compensation for drift is easily accomplished by a manual control on the control panel without affecting the span calibration.

Various modifications of the invention in addition to those shown and described herein will become apparent to those skilled in the art from the foregoing description and accompanying drawings. Such modifications are intended to fall within the scope of the appended claims.

What is claimed is:

1. A non-dispersive infrared gas analyzer, comprising, a sample cell for containing the gas mixture to be analyzed, means for directing infrared energy through said sample cell, means for periodically interrupting the infrared energy at a predetermined frequency, detector means responsive to the infrared energy at at least one preselected wavelength to produce an AC signal having an amplitude proportional to the infrared energy passing through said sample cell and having a frequency corresponding to the predetermined frequency, said preselected wavelength corresponding to the characteristic absorption wavelength of a preselected gas, and signal processing means for processing the AC signal output of said detector means to produce a DC signal having an amplitude proportional to the concentration of the preselected gas in the mixture being analyzed, said signal processing means including an output amplifier and first variable control means manually adjustable to adjust the gain of said output amplifier to bring the output of said output amplifier to zero with a non-absorbing gas in said sample cell, and second variable control means connected in a feedback loop to said output amplifier for span calibration.

2. A gas analyzer according to claim 1 wherein said signal processing means include full wave rectifier means for rectifying the AC signal produced by said detector means, said output amplifier being connected to said full wave rectifier means, said output amplifier having an input and an output, said first variable control means comprising a variable resistor series connected between said full wave rectifier means and said amplifying means.

3. A gas analyzer according to claim 1 wherein said second variable control means comprise a variable resistor series connected between the output of said output amplifier and the input thereof.

4. A gas analyzer according to claim 1 including a summing junction, means connecting said summing junction to the input of said output amplifier, first summing resistor means connected from said summing junction to said first variable control means, a source of reference potential opposite in polarity to that at the junction between said first summing resistor and said first variable control means, and second summing resistor means series connected from said summing junction to said source of reference potential.

5. A gas analyzer according to claim 1 wherein said signal processing means include first and second summing resistor means series connected in stated order between said first variable control means and a source of reference potential opposite in polarity to that at the junction between said first summing resistor means and said first control means, means connecting the junction between said first and second summing resistors to the input of said output amplifier, said second variable control means comprising a variable feedback resistor connecting the output of said output amplifier to the input thereof.

6. A gas analyzer according to claim 1 wherein said sample cell includes a removable portion comprising a cylindrical tube and a pair of windows at each end transparent to infrared energy, and wherein means are provided for resiliently and removably supporting said tube in said gas analyzer.

7. A gas analyzer according to claim 6 wherein said supporting means comprise a pair of resilient clips for engaging said cylindrical tube at regions spaced axially along said tube.

8. A gas analyzer according to claim 6 wherein said supporting means include means for locating the axial position of said sample cell with respect to said energy directing means and said detector means.

9. A non-dispersive infrared gas analyzer, comprising, a sample cell for containing the gas mixture to be analyzed, means for directing infrared energy through said sample cell, means for periodically interrupting the infrared energy at a predetermined frequency, detector means responsive to the infrared energy at at least one preselected wavelength to produce an AC signal having an amplitude proportional to the infrared energy passing through said sample cell and having a frequency corresponding to the predetermined frequency, said preselected wavelength corresponding to the characteristic absorption wavelength of a preselected gas, and signal processing means for processing the AC signal output of said detector means to produce a DC signal having an amplitude proportional to the concentration of the preselected gas in the mixture being analyzed, said signal processing means including an output amplifier, a voltage biasing network including a summing junction connected to the input of said output amplifier, first variable control means manually adjustable to bring the voltage at said summing junction to zero in the presence of a non-absorbing gas in said sample cell, and second variable control means connected in a feedback loop from the output of said output amplifier to the input thereof for span calibration.

10. A gas analyzer according to claim 9 wherein said signal processing means include full wave rectifier means for rectifying the AC signal produced by said detector means, said output amplifier being connected to said full wave rectifier means, said first variable control means comprising a variable resistor series connected between said full wave rectifier means and said output amplifier.

11. A gas analyzer according to claim 10 wherein said second variable control means comprise a variable resistor series connected between the output of said output amplifier and the input thereof.

* * * * *